United States Patent [19]

Eaton et al.

[11] Patent Number: 5,043,383
[45] Date of Patent: Aug. 27, 1991

[54] HEAT-SHRINKABLE FILM HAVING HIGH SHRINKAGE UPON BRIEF EXPOSURE TO LOW ACTIVATION TEMPERATURES

[75] Inventors: Bradley W. Eaton; Leigh E. Wood, both of St. Paul, Minn.

[73] Assignee: Minnestoa Mining and Manufacturing Company, St. Paul, Minn.

[21] Appl. No.: 438,360

[22] Filed: Nov. 17, 1989

[51] Int. Cl.$^5$ .................. C08L 29/04; C08L 53/02
[52] U.S. Cl. ........................ 525/57; 264/10.1; 525/60
[58] Field of Search .............. 525/57, 60; 264/20, 264/9.5, 210.1, 210.7

[56] References Cited

U.S. PATENT DOCUMENTS

| Re. 28,688 | 1/1976 | Cook | 260/4 |
|---|---|---|---|
| 3,562,356 | 2/1971 | Nyberg | 260/876 |
| 3,819,401 | 6/1974 | Massengale et al. | 156/85 |
| 3,912,565 | 10/1975 | Koch et al. | 156/85 |
| 4,247,584 | 1/1981 | Widiger et al. | 428/35 |
| 4,303,571 | 12/1981 | Jansen et al. | 260/33.6 AQ |
| 4,337,771 | 7/1982 | Pieniak | 128/287 |
| 4,386,125 | 5/1983 | Shiraki et al. | 428/36 |
| 4,476,180 | 10/1984 | Wnuk | 428/220 |
| 4,515,595 | 5/1985 | Kievit et al. | 604/385 A |
| 4,596,728 | 6/1986 | Yang | 428/36 |
| 4,705,657 | 11/1987 | Poulin | 264/22 |
| 4,820,590 | 4/1989 | Hodgson et al. | 428/516 |

FOREIGN PATENT DOCUMENTS 2160473A 5/1985 United Kingdom .

*Primary Examiner*—Allan M. Lieberman
*Attorney, Agent, or Firm*—Gary L. Griswold; Roger R. Tamte; William J. Bond

[57] ABSTRACT

Disposable diapers can be manufactured at high production speeds by using for the waistband a heat-shrinkable plastic film that is dimensionally stable at ordinary room temperature and shrinks in one direction at least 25% within 5 seconds at 54° C. Such a heat-shrinkable plastic film can be made by uniaxially cold-stretching a thin extrudate of a blend of an EVA copolymer and an (A-B) block copolymer of polystyrene and polyisoprene.

10 Claims, 1 Drawing Sheet

HEAT-SHRINKABLE FILM HAVING HIGH SHRINKAGE UPON BRIEF EXPOSURE TO LOW ACTIVATION TEMPERATURES

BACKGROUND OF THE INVENTION

1. Field of the Invention

The invention concerns heat-shrinkable plastic films and more specifically is concerned with disposable diapers that employ such films for such purposes as elastic waist bands.

2. Description of the Related Art

Disposable diapers typically include a liquid-permeable skin-contacting layer, a liquid-impermeable outer shell, and an intermediate absorbent element. In the manufacture of some disposable diapers, strips of heat-shrinkable plastic film are adhesively bonded to the outer shell and then heated to cause them to contract to form shirred, elastic waistband and leg openings. Typically, the outer shell is a thin film of polyethylene which would become distorted if exposed to high temperatures, but at temperatures low enough not to distort the polyethylene film, known heat-shrinkable plastic films contract slowly and hence can require diaper-manufacturing lines to be operated at slower speeds than otherwise would be feasible.

U.S. Pat. No. 4,563,185 (Reiter) describes at length known techniques for applying strips that are contractible, e.g., by heat, to impart both shirring and elasticization at the waistband and/or leg openings of a disposable diaper. The strip employed by Reiter at the waistband is "ethylene propylene rubber blended with ethylene vinyl acetate" (col. 14, lines 30-32) which Reiter says (col. 7, lines 53-62) is described in U.S. Pat. No. 4,303,571 (Jansen et al.). The Jansen patent says that uniaxial orientation of a film of this composition renders it heat-shrinkable, and that exposure of the oriented film to heat results in a return to the unoriented state and the original elastic properties.

U.S. Pat. No. 4,337,771 (Pieniak et al.) describes a film, strips of which are useful for providing shirred waistbands and leg openings. "The strip is intermittently secured to the backing and/or facing in the central portion of the diaper margin to maintain its elasticity; however, the end portions of the strip are continuously . . . secured at the corner portions of the diaper whereby the previously elastic end portions of the strip are effectively rendered inelastic, and the strip reinforces the diaper in such regions" (col. 2, lines 30-39). The strip, usually called an "elastic film member," preferably is made from compositions of A-B-A or A-B block copolymers wherein the A-blocks can be derived from styrene and the B-blocks are derived from conjugated dienes or lower alkenes, which compositions include low-molecular-weight modifiers such as amorphous polypropylene. The elastic film member can be made from a material that becomes elastic when heat shrunk such as a polyolefin or a copolymer of ethylene and vinyl acetate. Upon being secured to the facing and/or backing of the diaper by ultrasonic welding, the elastic film member "is heated at its end portions to a point where it almost melts and loses substantially all of its memory and is thus non-elastic in those areas" (col. 11, lines 2-12).

U.S Pat. No. 4,515,595 (Kievit et al.) describes a disposable diaper with a waistband that can be made elastic by affixing an elastic member or tape made from natural rubber. The elastic member can be stretched to an elongated orientation, affixed to the diaper, and then contracted (e.g., by heating) to gather the diaper material adjacent the elastic member.

U.S. Pat. No. 4,476,180 (Wnuk) describes elastic films made from blends of an elastomeric linear triblock copolymer and ethylene/vinyl acetate (EVA) copolymer. Preferably the end blocks of the elastomeric copolymer are polystyrene, and preferred interior blocks are polybutadiene and polyisoprene. The melt index of the elastomeric block copolymer of Wnuk's elastic films is less than about 10 (Cond. E of ASTM Method D 1238) and that of the EVA copolymer is less than about 0.6 (Cond. B). These elastic films are made from about 40% to about 80% of the elastomeric block copolymer and about 20% to 60% of the EVA copolymer.

Wnuk's elastic films "may be used in a wide variety of applications where a thin, elastic material would be useful. Such films are particularly useful as low cost elastic members for disposable wearing apparel such as diapers and incontinent briefs; they may be used as leg bands or waist bands" (col. 6, lines 41-45). An elastic film of the Wnuk patent has low permanent set in a test wherein the film is stretched to twice its original length, held at that extension for 10 minutes at room temperature and then allowed to relax. In that test, films of Wnuk's examples have a permanent set of from 12 to 24%.

The Wnuk patent also teaches that the elastic films can be made nonblocking "by loading the film surface with small particles or powders such as chalk, clay, silica, and similar materials" in amounts from about 0.5 $g/m^2$ to about 5 $g/m^2$ (col. 4, lines 18-29).

U.S. Pat. No. 3,562,356 (Nyberg et al.) describes elastic films made from blends, among which are an elastomeric linear triblock copolymer such as a polystyrene-polybutadiene-polystyrene copolymer and an EVA copolymer. The Nyberg patent says: "Other benefits of the blends as compared with the unmodified block copolymers include the improved resistance of molded articles to distortion and shrinkage at elevated temperatures" (col. 4, lines 51-55).

SUMMARY OF THE INVENTION

The invention should permit disposable diapers to be manufactured at higher production speeds and lower energy consumption than have heretofore been feasible by using for the waistband a heat-shrinkable plastic film which is believed to be the first that is dimensionally stable at ordinary room temperatures and shrinks in one direction at least 25% within 5 seconds at 54° C. (130° F). This heat-shrinkable plastic film is believed to be novel, and its extraordinary heat-shrinkability at that moderately elevated temperature is surprising, considering that it is chemically similar to Nyberg's elastic films which resist shrinkage at elevated temperatures and to Wnuk's films which have low permanent set as opposed to the high permanent set of the novel heat-shrinkable plastic film when cold-drawn (cold-stretched) either at room temperature or at moderately elevated temperatures.

Briefly, the heat-shrinkable plastic film of the present invention is obtained by uniaxially cold-stretching (cold-drawing) to a length of at least 3× its original dimension a thin extrudate of a blend of from 40 to 85 parts by weight of an EVA copolymer
    having a vinyl acetate content of from 10% to 50%
    and a melt index of from 1 to 100 (Cond. E of ASTM Method D 1238), and correspondingly from 60 to 15 parts by weight of an (A-B) linear or radial block copolymer where A is polystyrene and B is selected from polyisoprene, polybutadiene, and poly(ethylenebutylene), which copolymer has an A-block content of from 10 to 45% and a melt index of from 0.1 to 25 (Cond. G).

By "uniaxially cold-stretching" is meant that the extrudate is stretched in one direction at a temperature well below its softening point. The cold-stretching preferably is carried out at a temperature from 40° to 50° C. If the cold-stretching temperature were much below 40° C., the extrudate might break at the preferred degree of cold-stretching, i.e., at 4× to 5.5×. When stretched to that preferred extent within that preferred temperature range, the resulting heat-shrinkable films have excellent shrinkability at 54° C., with very little risk of breakage when made of preferred blends of EVA copolymer and (A-B) block copolymer. Significantly higher cold-stretching ratios are not recommended, because an unsupported extrudate might break at 6× or higher. On the other hand, cold-stretching at less than 4× may not afford desirably high shrinkage within 5 seconds at 54° C.

When the cold-stretching temperature exceeds 50° C., the cold-stretched film tends to have better permanent set (that is, less springback) but also tends to shrink to a lesser extent within 5 seconds at 54° C. than does a film that has been cold-stretched at a temperature with the aforementioned preferred range of 40°–50° C.

Lower cold-stretching temperatures can be employed and a somewhat higher degree of cold-stretching can be achieved when the extrudate is supported by two adhered surface layers of polyolefin such as polyethylene, polypropylene, or a blend of polyethylene or polypropylene with another polyolefin. Those surface layers also afford nonblocking surfaces. In the absence of such surface layers, the blend to be cold-stretched preferably incorporates an anti-blocking agent, or slip agent, e.g., finely divided calcium carbonate, diatomaceous earth, and erucamide in amounts from about 1 to 10% by weight of the film. Significantly larger amounts might prevent a thin extrudate from being cold-stretched at least 3× without breaking.

Whether or not the novel heat-shrinkable film has surface layers, it preferably is quenched immediately following cold-stretching in order to lock it into a thermodynamically-unstable, oriented configuration.

For use as waistbands in the manufacture of disposable diapers, it would be preferred to perform the uniaxial cold-stretching in the crosswise direction of a long supply roll, were it not for the higher cost of doing so versus lengthwise orientation which is more economical, because crosswise orientation requires the use of relatively expensive tentering equipment and involves waste where the cold-stretched film is marred by the tenter hooks. However, when a roll of lengthwise oriented film is cut into strips to be used as diaper waistbands, it may be necessary to rotate the individual strips 90° to make them extend in the crosswise direction of the diaper blank.

A roll of the novel heat-shrinkable film can bear an adhesive layer by which it can be adhered to a diaper blank. Then in conjunction with the conversion of that diaper blank into disposable diapers, the heat-shrinkable film is cut into short lengths, each of which is adhered by its adhesive layer to the outer shell of the diaper blank. Instead of being precoated with an adhesive layer, the uniaxially cold-stretched film can be coated with adhesive while being unwound from the supply roll.

THE DRAWING

The invention may be more easily understood in reference to the drawing in which FIG. 1 is a schematic representation of apparatus for uniaxially cold-stretching a thin extrudate to convert it into a heat-shrinkable plastic film of the invention; and FIG. 2 shows a diaper blank that incorporates at each of its waistband and leg openings a pair of strips of the heat-shrinkable plastic film made as in FIG. 1.

In the apparatus of FIG. 1, a thin, unoriented plastic extrudate 10 is unwound from a roll 12 and drawn through a first pair of nip rolls 14 (steel) and 15 (rubber covered) and four heated idler rolls 16 over which the extrudate is stretched at least 3× in the lengthwise direction due to faster rotation of a second pair of nip rolls 18 (steel) and 19 (rubber covered). Each of the four idler rolls is internally heated to keep its surface temperature within the range of about 40°–50° C. The resulting cold-stretched, heat-shrinkable plastic film 20 is drawn across a water-cooled idler chill roll 22 at which the film is locked into a thermodynamically-unstable oriented configuration. From the second nip rolls 18 and 19, the heat-shrinkable film 20 travels to a slitter 24 at which it is slit to a useful width before being wound up on a winder 26.

In FIG. 2, a diaper blank 30 is shown with its skin-contacting layer 32 facing upwardly, beneath which are two strips 34 and 35 of the novel heat-shrinkable film at the waistbands and two strips 37 and 38 at the leg openings. The diaper blank 30 also includes an absorbent element 40 and a pair of adhesive closure tabs 42 and 43.

DETAILED DESCRIPTION

Figure 1:
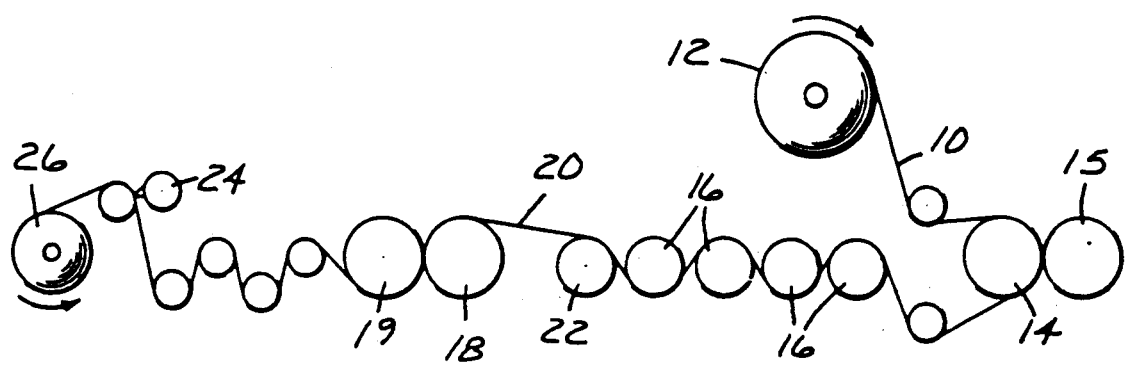
Figure 2:
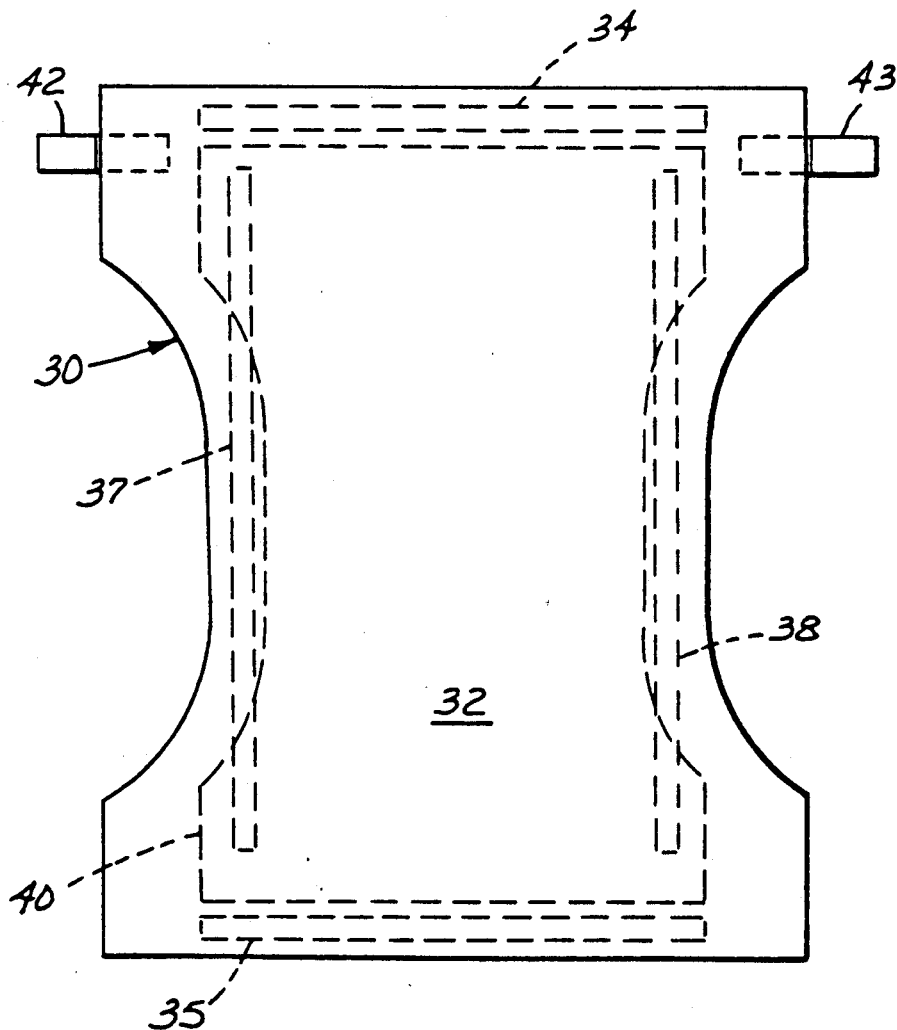

Preferred (A-B) block copolymers include linear A-B-A linear triblock copolymers such as "Kraton" D-1107, "Kraton" D-1101, "Kraton" D-1111, and "Kraton" G-1657 from Shell Chemical. Also preferred are radial (A-B) copolymers such as "Kraton" DX-1116 and "Kraton" DX-1184X and multiblock ABABA copolymers such as "Stereon" 840A from Firestone Synthetic Rubber and Latex Co.

Preferably the melt index of the (A-B) block copolymer is from 1 to 15 (Cond. G), more preferably from 3 to 10. When its melt index is substantially below 1, a blend with the EVA copolymer tends to be so viscous that it is difficult to form a thin extrudate to be cold-stretched. When its melt index is substantially above 15, it is difficult to cold-stretch a thin extrudate of the blend at least 3× without breaking.

Preferably the EvA copolymer has a vinyl acetate content of from 18% to 32%. At substantially below that preferred range, the novel cold-stretched plastic films tend to have less heat-shrinkage. At substantially above that preferred range, the heat-shrinkable plastic films have a tendency to block that cannot be fully offset by the use of anti-blocking agents without a significant reduction in strength and integrity.

Preferably the the EVA copolymer has a melt index of from 3 to 40 (Cond. E), more preferably from 5 to 30. A melt index of 5 (Cond. E) roughly corresponds to a melt index of 0.5 (Cond. B). When the EVA copolymer has a melt index substantially below 5 (Cond. E), a blend with the (A-B) block copolymer is difficult to extrude, and this limits the line speed at which a heat-shrinkable film can be produced. When the melt index of the EVA copolymer is substantially above 30, the blend may lack sufficient tensile strength to be cold-stretched at least 3× without danger of breakage.

Because the current cost of the EVA copolymer is about 40% less than that of the (A-B) block copolymer, economy suggests that the ratio of EVA copolymer to block copolymer should be as high as possible as long as quality is not sacrificed. This can be accomplished when that ratio is between 3:1 and 5:1.

Preferred heat-shrinkable plastic films of the invention undergo 40-50% unidirectional shrinkage upon exposure to 54° C. for 5 seconds. Cold-stretched films having such high shrinkage have been made when the ratio of the EVA copolymer to the (A-B) block copolymer is from 2:1 to 5:1. When that ratio is substantially higher that 5:1, there is a danger of a thin extrudate breaking upon being cold-stretched to 3× or greater. When that ratio is substantially below 2:1, the cold-stretched film might not have the high permanent set necessary to afford the desired degree of heat-shrinkability.

Heat-Shrinkage Value

A long strip ⅝ inch (1.6 cm) in width is inked to provide two marks, 10 cm apart. After being immersed in water at 54° C. for 5 seconds, the strip is removed and the distance between the marks is measured. Its Heat-Shrinkage Value is the ratio of the reduction in length (i.e., original length minus shrunk length) to the original length, expressed as a percent.

In the following examples, all parts are given by weight.

EXAMPLES 1-4

Blends were made using
- an EVA copolymer ("Elvax" 260 from E. I. duPont) which has a vinyl acetate content of 28% and a melt index (Cond. E) of 6;
- a linear (A-B) block copolymer ("Kraton" 1111 from Shell Chemical Co.) of polystyrene and polyisoprene having polystyrene end blocks, which has a styrene content of 21% and a melt index (Cond. G) of 3;
- a linear (A-B) block copolymer ("Kraton" 1107 from Shell Chemical Co.) of polystyrene and polyisoprene having polystyrene end blocks, which has a styrene content of 14% and a melt index (Cond. G) of 9; and
- $CaCO_3$, a particulate anti-block agent in a polyethylene carrier resin (CBE 13782E from C. B. Edwards & Co., Minneapolis, Mn.). The parts by weight of each are indicated in Table I.

TABLE I

| Example | 1 | 2 | 3 | 4 |
|---|---|---|---|---|
| "Kraton" 1107 | 45.0 | 37.5 | | |
| "Kraton" 1111 | | | 47.5 | 37.5 |
| "Elvax" 260 | 45.0 | 55.0 | 47.5 | 55.0 |
| CBE 13782E | 10.0 | 7.5 | 5.0 | 7.5 |

Each of these blends was extruded to a thickness of about 0.125 mm. The extrudate later was unwound and oriented between two sets of nip rolls between which it was heated by infrared lamps. In doing so, the width of the extrudate necked down from about 15.2 to 7.6 cm. The temperature to which the extrudate was heated was not measured but was believed to be on the order of 60° C. The degree to which each of the extrudates was thus cold-stretched is reported in Table II, together with the Heat-Shrinkage Value for each of the resulting films.

TABLE II

| Example | Draw Ratio | Heat-Shrinkage Value (%) |
|---|---|---|
| 1 | 5:1 | 21 |
|   | 5.5:1 | 26 |
|   | 6:1 | 26 |
| 2 | 5.5:1 | 26 |
|   | 6:1 | 28 |
| 3 | 5:1 | 30 |
|   | 5.5:1 | 34 |
|   | 6:1 | 40 |
|   | 6.5:1 | 35 |
| 4 | 5:1 | 34 |
|   | 5.5:1 | 33 |
|   | 6:1 | 44 |
|   | 6.5:1 | 45 |

EXAMPLES 5-9

Blends were prepared as in Example 1 and also employing two other EVA copolymers:

| | vinyl acetate content | melt index (Cond. E) |
|---|---|---|
| "Elvax" 450 | 18% | 8 |
| "Elvax" 660 | 12% | 2.5 |

Also including in the blends were erucamide, a fatty acid slip agent, namely, "Ampacet" 10110 from Ampacet Corp.; an antioxidant, namely "Irganox" 1076 from Ciba-Geigy; and a pigment, namely a blend of equal parts of $TiO_2$ and polypropylene. The compositions of the blends are noted in Table III.

TABLE III

| Example | 5 | 6 | 7 | 8 | 9 |
|---|---|---|---|---|---|
| "Kraton" 1111 | 35.0 | 25.0 | 25.0 | 25.0 | 25.0 |
| "Elvax" 260 | 55.0 | 60.0 | | | 30.0 |
| "Elvax" 450 | | | 60.0 | | 30.0 |
| "Elvax" 660 | | | | 60.0 | |
| CBE 13782E | 7.0 | 9.0 | 9.0 | 9.0 | 9.0 |
| Slip agent | 2.0 | 2.0 | 2.0 | 2.0 | 2.0 |
| Antioxidant | 1.0 | 1.0 | 1.0 | 1.0 | 1.0 |
| Pigment | | 3.0 | 3.0 | 3.0 | 3.0 |

Each of these blends were extruded and then oriented on apparatus as illustrated in FIG. 1 with the heated rolls having a surface temperature of about 46° C. The degree of cold-stretching of each is reported in Table IV, together with the Heat-Shrinkage Value for each of the resulting films.

TABLE IV

| Example | Draw Ratio | Heat-Shrinkage Value (%) |
|---|---|---|
| 5 | 5:1 | 50 |
|   | 5.5:1 | 50 |
|   | 6:1 | 49 |
| 6 | 5:1 | 53 |
|   | 5.5:1 | 52 |
| 7 | 5:1 | 39 |
|   | 5.5:1 | 43 |
| 8 | 5:1 | 34 |
|   | 5.5:1 | 40 |
| 9 | 5:1 | 48 |
|   | 5.5:1 | 50 |

We claim:

1. Heat-shrinkable film comprising a blend of from 40 to 85 parts by weight of an EVA copolymer having a vinyl acetate content of from about 10% to 50% and a melt index of from about 1 to 100 (Cond. E of ASTM Method D 1238), and correspondingly from 60 to 15 parts by weight of an (A-B) block copolymer where A is polystyrene and B is selected from polyisoprene, polybutadiene, and poly(ethylenebutylene) wherein the (A-B) copolymer has an A-block content of from about 10% to 45% and a melt index of from about 0.1 to 25 (Cond. G), which film has been uniaxially cold-stretched at least 3×, and shrinks in the stretched direction at least 25% within 5 seconds at 54° C.

2. Heat-shrinkable film as defined in claim 1 that has been uniaxially cold-stretched from 4× to 5.5×.

3. Heat-shrinkable film as defined in claim 1 that has been uniaxially cold-stretched at a temperature from 40° to 50° C.

4. Heat-shrinkable film as defined in claim 1 that has been uniaxially cold-stretched in the lengthwise direction and then would upon itself in roll form.

5. Heat-shrinkable film as defined in claim 1 wherein the ratio of EVA to block copolymer is from 2:1 to 5:1 by weight.

6. Heat-shrinkable film as defined in claim 1 wherein the EVA copolymer has a vinyl acetate content of from 18% to 32%.

7. Heat-shrinkable film as defined in claim 1 wherein the EVA copolymer has a melt index of from 3 to 40 (Cond. E).

8. Heat-shrinkable film as defined in claim 1 wherein the melt index of the (A-B) block copolymer is from 1 to 15 (Cond. G).

9. A think extrudate that becomes heat-shrinkable when uniaxially cold-stretched at least 3×, which extrudate comprises a blend of an EVA copolymer having vinyl acetate content of from 15% to 50% and a melt index of from 1 to 100 (Cond. E of ASTM Method D 1238), and an (A-B) block copolymer where A is polystyrene, and B is selected from polyisoprene, polybutadiene, and poly(ethylenebutylene), which copolymer has an A-block content of from 10% to 45% and a melt index of from 0.1 to 25 (Cond. G), and the ratio of the EVA copolymer to the (A-B) block copolymer being from 2:1 to 5:1 by weight.

10. A thin extrudate as defined in claim 9 wherein the EVA copolymer has a vinyl acetate content of from 18% to 32%.

* * * * *

UNITED STATES PATENT AND TRADEMARK OFFICE
CERTIFICATE OF CORRECTION

PATENT NO. : 5,043,383

DATED : August 27, 1991

INVENTOR(S) : Bradley W. Eaton and Leigh E. Wood

It is certified that error appears in the above-identified patent and that said Letters Patent is hereby corrected as shown below:

Column 7, line 29, delete "would" and insert --wound--.

Column 8, line 13, delete "think" and insert --thin--.

Signed and Sealed this

Eighth Day of June, 1993

Attest:

MICHAEL K. KIRK

*Attesting Officer*   Acting Commissioner of Patents and Trademarks